US012810061B1

(12) United States Patent
Weingarden et al.

(10) Patent No.: US 12,810,061 B1
(45) Date of Patent: Nov. 24, 2026

(54) METHODS AND PLATFORMS FOR CONTROLLING PRODUCTION OF PLAIN LANGUAGE SUMMARIES USING GENERATIVE AI

(71) Applicant: TrialAssure Inc., Canton, MI (US)

(72) Inventors: Zachary Thomas Weingarden, Grosse Pointe Woods, MI (US); Jin Seuk Park, Canton, MI (US); Mohamad Hani Zahreddine, Dearborn Heights, MI (US)

(73) Assignee: TrialAssure Inc., Canton, MI (US)

( * ) Notice: Subject to any disclaimer, the term of this patent is extended or adjusted under 35 U.S.C. 154(b) by 243 days.

(21) Appl. No.: 18/786,338

(22) Filed: Jul. 26, 2024

Related U.S. Application Data

(60) Provisional application No. 63/529,120, filed on Jul. 26, 2023.

(51) Int. Cl.
*G06F 40/186* (2020.01)
*G06F 40/197* (2020.01)
*G16H 10/20* (2018.01)

(52) U.S. Cl.
CPC .......... *G06F 40/186* (2020.01); *G06F 40/197* (2020.01); *G16H 10/20* (2018.01)

(58) Field of Classification Search
CPC ...... G06F 40/186; G06F 40/197; G16H 10/20
See application file for complete search history.

(56) References Cited

U.S. PATENT DOCUMENTS

| | | | |
|---|---|---|---|
| 9,507,862 B2 | 11/2016 | Chennai et al. | |
| 9,773,124 B2 | 9/2017 | El Emam et al. | |
| 11,347,891 B2 | 5/2022 | Raphael et al. | |
| 12,481,773 B2 | 11/2025 | Park et al. | |

(Continued)

FOREIGN PATENT DOCUMENTS

| | | | |
|---|---|---|---|
| CA | 2870930 A1 | 5/2015 | |

OTHER PUBLICATIONS

Fenz, S., Heuirx, J., Neubauer, T., & Rella A., "De-identification of unstructured paper-based health records for privacy-preserving secondary use." Journal of Medical Engineering & Technology, 38:5, pp. 260-268, 2014 (10 pages).

(Continued)

*Primary Examiner* — Haoshian Shih
(74) *Attorney, Agent, or Firm* — TILLMAN WRIGHT, PLLC; Neal Wolgin; David R. Higgins

(57) ABSTRACT

A method of using a software platform to control an AI interface to produce plain language summaries (PLSs) for clinical trial data sources includes creating, editing, and managing a library of PLS output document templates, creating, editing, and managing a library of dynamic AI-text tags (including identifier and prompt) for use in the PLS output document templates, selecting a PLS output document template for producing a PLS output document for designated input clinical trial source data, and generating the PLS document by processing the PLS output document template and the dynamic AI-text tags therein using an AI engine with language model. The input clinical trial source data is retrieved from a repository and provided to the AI engine or uploaded by a user, in a structure or unstructured data format, and indexed for interrogation by the AI engine.

18 Claims, 10 Drawing Sheets

(56) References Cited

U.S. PATENT DOCUMENTS

| | | | | |
|---|---|---|---|---|
| 2008/0240425 | A1 | 10/2008 | Rosales et al. | |
| 2016/0342812 | A1 | 11/2016 | Lynch et al. | |
| 2020/0065524 | A1 | 2/2020 | Carlson | |
| 2022/0058339 | A1* | 2/2022 | Archuleta | G06F 40/117 |
| 2023/0195916 | A1 | 6/2023 | Park et al. | |
| 2025/0378106 | A1* | 12/2025 | Manivannan | G06F 16/358 |

OTHER PUBLICATIONS

El Emam, K., and Abdallah K., "De-identifying Data in Clinical Trials." Applied Clinical Trials, vol. 24, Issue 8, Aug. 1, 2015 (26 pages).

* cited by examiner

100

200

400

400

400

METHODS AND PLATFORMS FOR CONTROLLING PRODUCTION OF PLAIN LANGUAGE SUMMARIES USING GENERATIVE AI

CROSS-REFERENCE TO RELATED APPLICATION

For purposes of the United States, the present application is a U.S. nonprovisional patent application of, and claims priority under 35 U.S.C. § 119(e) to, U.S. provisional patent application Ser. No. 63/529,120, filed Jul. 26, 2023, and entitled, "PLAIN LANGUAGE SUMMARY DRAFT GENERATION USING DATA SOURCE AND LANGUAGE MODEL," which '120 application is incorporated by reference herein in its entirety.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved

BACKGROUND OF THE PRESENT INVENTION

Field of the Present Invention

The present invention relates generally to plain language summaries of clinical trials, and, more particularly, to generating draft documents using tags corresponding to specified input source data and an AI engine and language model.

Background

In the field of healthcare in recent years, a variety of entities recognized the important of disseminating information to the general public about the latest treatments, studies, and developments in the field. In particular, increased emphasis has been placed on transforming complicated medical information from clinical trials and the like into simple, easy-to-understand language suitable for most people to digest. For example, drug companies publish the results of their clinical trials in medical journals, but these publications are difficult to access and even more difficult for the layperson to read.

Increasingly, various entities have made use of plain language summaries (PLSs) (also called layperson summaries, lay summaries, lay language summaries, simple summaries, and trial results summaries, depending on the context or the like) to make the clinical results of clinical studies more readily available to a much wider audience, including to patients, prospective trial participants, healthcare providers, caregivers, researchers, and others. A PLS is a straightforward document, typically written to a $6^{th}$ grade level, that briefly explains the who, what, where, when, why, and how of a clinical trial, including everything from what is being accomplished in the trial to the results of the trial to the type of placebo used in the trial.

Although PLSs have been in use for some time, they are becoming more of an expectation, or even a requirement, with respect to clinical trials. Unfortunately, preparation of a PLS is almost entirely a time-consuming manual process, and must be carried out by a trained medical writer. Furthermore, although guidelines are often used for the generation of PLSs, typographical errors are often made, important information is often accidentally omitted, and other errors creep into the finished documents.

As with a huge variety of other areas, generative artificial intelligence (AI) technology shows promise in carrying out the process of converting complicated technical information related to clinical trials into more readily understood PLSs. However, a conventional process of assessing a clinical trial data source, feeding relevant portions of the data source to an AI engine, managing the results from the AI engine, and producing a PLS based on those results remains complicated and produces inconsistent output.

Thus, a need exists for a technological solution that increases efficiency, decreases the time required, ensures a process is followed, reduces errors, improves the overall quality of the finished product, facilitates consistency, and/or the like, when using generative AI technology to prepare plain language summaries for clinical trials. One or more of the foregoing needs and/or other needs may be addressed by one or more aspects of the present invention.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

The present invention includes many aspects and features. Moreover, while many aspects and features relate to, and are described in, the context of plain language summaries of clinical trials, the present invention is not limited to use only in such a context, as will become apparent from the following summaries and detailed descriptions of aspects, features, and one or more embodiments of the present invention.

Broadly defined, the present invention according to one aspect relates to a method providing a technical solution to the technical problem of using a software platform to control an artificial intelligence (AI) interface to produce plain language summaries (PLSs) for clinical trial data sources, including: effecting display, to a first user who has utilized a web browser loaded on a first device to navigate to a uniform resource locator, of a PLS template management interface prompting the first user to create a template for a PLS; receiving data corresponding to input by the first user corresponding to creation of a first PLS output document template; creating the first PLS output document template based on the received data; effecting display, to the first user in the web browser loaded on the first device, of an editor tool for editing the first PLS output document template; receiving data corresponding to input by the first user defining fields and sections of the first PLS output document template; effecting display, to a second user who has utilized a web browser loaded on a second device to navigate to a uniform resource locator, of a dynamic tag management interface, for managing placeholder tags for AI-generated text, prompting the second user to create a dynamic AI-text tag for use in PLS output document templates; receiving data corresponding to input by the second user corresponding to creation of a first dynamic AI-text tag; creating the first dynamic AI-text tag based on the received data; effecting display, to the second user in the web browser loaded on the second device, of an editor tool for configuring the first dynamic AI-text tag; receiving data corresponding to input by the second user defining a parameter set for the first dynamic AI-text tag, the parameter set including at least a unique tag identifier and an AI prompt; storing the first dynamic AI-text tag for subsequent use in PLS output document templates for producing PLSs for clinical trial data sources; while effecting display, to the first user in the web browser loaded on the first device, of the editor tool for editing the first PLS output document template, prompting the first user to select one or more dynamic AI-text tags for adding to the first PLS output document template; receiving data corresponding to input by the first user selecting at least the first dynamic AI-text tag and placing it a first location in the first PLS output document template; adding the one or more dynamic AI-text tags, including the first dynamic AI-text tag, to the first PLS output document template in the first location in the first PLS output document template; storing the first PLS output document template for subsequent use in producing PLSs for clinical trial data sources; effecting display, to a third user who has utilized a web browser loaded on a third device to navigate to a uniform resource locator, of a PLS document creation interface prompting the third user to initiate a PLS output document; receiving data corresponding to input by the third user corresponding to initiation of a first PLS output document; creating the first PLS output document based on the received data; effecting display, to the third user in the web browser loaded on the third device, of an editor tool for prompting the third user to identify input clinical trial source data and select a PLS output document template for the first PLS output document; receiving data corresponding to input by the third user identifying designated input clinical trial source data and selecting the first PLS output document template for the first PLS output document; receiving data corresponding to instruction by the third user to generate the first PLS output document; thereafter, generating a draft of the first PLS output document, wherein such generating step includes, for each of the one or more dynamic AI-text tags in the first PLS output document template: (i) sending the AI prompt to an AI engine with language model, (ii) via the AI engine with language model, processing the AI prompt against the designated input clinical trial source data to generate draft plain language for use in the draft of the first PLS output document, (iii) returning the generated draft plain language from the AI engine with language model, and (iv) replacing the respective dynamic AI-text tag in the draft of the first PLS output document with the draft plain language returned from the AI engine with language model; and effecting display, to the third user in the web browser loaded on the third device, of a completed version of the draft first PLS output document.

In a feature of this aspect, the first user and the second user are the same user.

In another feature of this aspect, the first user and the third user are the same user.

In another feature of this aspect, the method further includes steps of: effecting display, to the second user who has utilized a web browser loaded on the second device to navigate to a uniform resource locator, of the dynamic tag management interface, for managing placeholder tags for AI-generated text, prompting the second user to create additional dynamic AI-text tags for use in PLS output document templates; receiving data corresponding to input by the second user corresponding to creation of additional dynamic AI-text tags; creating the additional dynamic AI-text tags based on the received data; effecting display, to the second user in the web browser loaded on the second device, of the editor tool for configuring the additional dynamic AI-text tags; receiving data corresponding to input by the second user defining a parameter set for each of the additional dynamic AI-text tags, each respective parameter set including at least a unique tag identifier and an AI prompt; storing the additional dynamic AI-text tags for subsequent use in PLS output document templates for producing PLSs for clinical trial data sources; and effecting display, to the first user in the web browser loaded on the first device, a library of stored dynamic AI-text tags for use by the first user in selecting the one or more dynamic AI-text tags for adding to the first PLS output document template.

In another feature of this aspect, the method further includes effecting display, to a fourth user who has utilized a web browser loaded on a fourth device to navigate to a uniform resource locator, of the PLS document creation interface prompting the fourth user to initiate a PLS output document; receiving data corresponding to input by the fourth user corresponding to initiation of a second PLS output document; creating the second PLS output document based on the received data; effecting display, to the fourth user in the web browser loaded on the fourth device, of the editor tool for prompting the fourth user to identify input clinical trial source data and select a PLS output document template for the second PLS output document; receiving data corresponding to input by the fourth user identifying designated input clinical trial source data and selecting the first PLS output document template for the second PLS output document; receiving data corresponding to instruction by the fourth user to generate the second PLS output document; thereafter, generating a draft of the second PLS output document by, wherein the generating step includes, for each of the one or more dynamic AI-text tags in the second PLS output document template: (i) sending the AI prompt to an AI engine with language model, (ii) via the AI engine with language model, processing the AI prompt against the designated input clinical trial source data to generate draft plain language for use in the draft of the second PLS output document, (iii) returning the generated draft plain language from the AI engine with language model, and (iv) replacing the respective dynamic AI-text tag in the draft of the second PLS output document with the draft plain language returned from the AI engine with language model; and effecting display, to the fourth user in the web browser loaded on the fourth device, of a completed version of the draft second PLS output document. In a further feature, the third user and the fourth user are the same user. In another further feature, the third user and the fourth user are different users.

In another feature of this aspect, the input clinical trial source data is structured data. In a further feature, the structured data is stored in a standardized format in a clinical trial data repository. In another further feature, the parameter set for each dynamic AI-text tag further includes a section of data from the structured input clinical trial source data, and wherein generating a draft of the first PLS output document further includes, for each of the one or more dynamic AI-text tags in the second PLS output document template, sending the section of data to the AI engine with language model as part of the AI prompt. In another further feature, the method further includes: effecting display, to the second user who has utilized a web browser loaded on the second device to navigate to a uniform resource locator, of a dynamic tag management interface, for managing placeholder tags for data-driven elements of the structured input clinical trial source data; prompting the second user to create a dynamic source data-driven tag for use in PLS output document templates; receiving data corresponding to input by the second user corresponding to creation of a first dynamic source data-driven tag; creating the first dynamic source data-driven tag based on the received data; effecting display, to the second user in the web browser loaded on the second device, of an editor tool for configuring the first dynamic source data-driven tag; receiving data corresponding to input by the second user defining a parameter set for the first dynamic source data-driven tag, the parameter set including at least a unique tag identifier and a specific structured element to be retrieved from the structured input clinical trial source data and substituted for the first dynamic source data-driven tag; storing the first dynamic source data-driven tag for subsequent use in PLS output document templates for producing PLSs for clinical trial data sources; and while effecting display, to the first user in the web browser loaded on the first device, of the editor tool for editing the first PLS output document template, prompting the first user to select one or more dynamic source data-driven tags for adding to the first PLS output document template. In another further feature, the step of generating the draft of the first PLS output document includes, for each of the one or more dynamic source data-driven tags in the first PLS output document template: (i) retrieving the specific structured element from the designated input clinical trial source data, and (ii) replacing the respective dynamic source data-driven tag in the draft of the first PLS output document with the retrieved structured element. In another further feature, the specific structured element is specific text, specific data, a specific graphic, or a specific image.

In another feature of this aspect, the input clinical trial source data is uploaded by the third user. In a further feature, the input clinical trial source data is unstructured data. In another further feature, the method further includes a step of indexing the uploaded input clinical trial source data and placing the indexed input clinical trial source data in a storage area accessible to the AI engine, and wherein generating a draft of the first PLS output document further includes, for each of the one or more dynamic AI-text tags in the second PLS output document template, querying the indexed input clinical trial source data by the AI engine with language model. In another further feature, the input clinical trial source data is in a document of a standard file type.

In another feature of this aspect, the first PLS output document template is one of a plurality of PLS output document templates stored in a library, and wherein the step of effecting display, to the third user in the web browser loaded on the third device, of an editor tool includes effecting display of the library of PLS output document templates for prompting the third user to select one of the PLS output document templates, of the plurality of PLS output document templates, for the first PLS output document.

Broadly defined, the present invention according to another aspect relates to a system for providing a technical solution to the technical problem of reliably preparing plain language summaries (PLS) of clinical trials by generating a draft PLS using a data source and a language model, including: a software platform, including a front-end graphical user interface (GUI) and a back-end database; one or more clinical trial data source; and an artificial intelligence (AI) engine using a language model; wherein the front-end graphical user interface (GUI) interactively displays, to a user, a document template that includes a plurality of dynamic tags, wherein each tag corresponds to a set of parameters for generating text via the AI engine, such as the prompt and specific data elements, and wherein the software platform replaces each tag in the document template with AI-generated text, drawn from the one or more clinical trial data source, based on the respective set of parameters, and displays, to the user, a draft document in the form of the document template but that includes the AI-generated text for each tag in place of the respective tag.

Further areas of applicability of the present invention will become apparent from the detailed description provided hereinafter. It should be understood that the detailed description and specific examples, while indicating preferred embodiment(s) of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
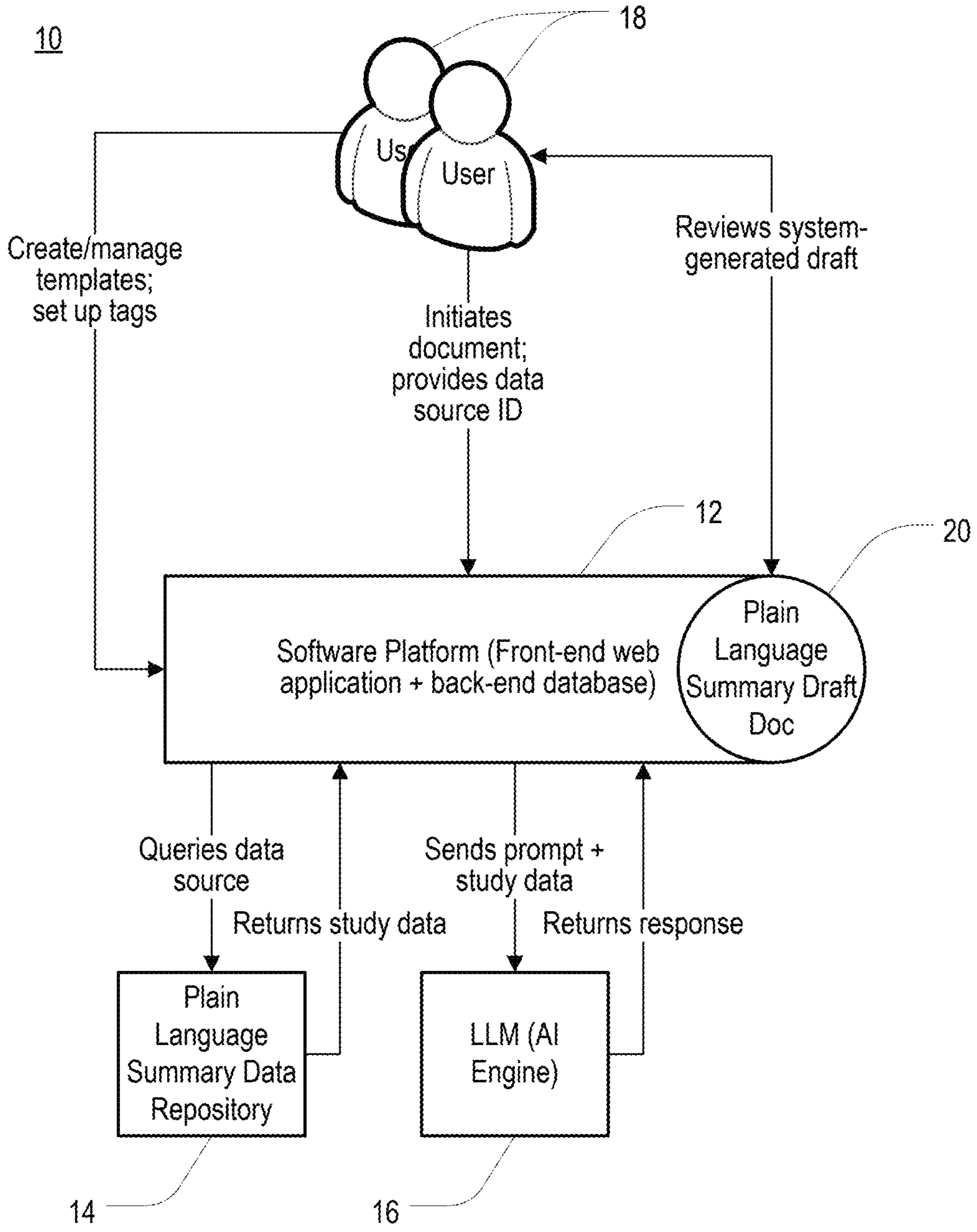
FIG. 1 is a high-level functional diagram of a system for plain language summary draft generation using a data source and a language model in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Furthermore, an embodiment of the invention may incorporate only one or a plurality of the aspects of the invention disclosed herein; only one or a plurality of the features disclosed herein; or combination thereof. Moreover, many embodiments, including adaptations, variations, modifications, and equivalent arrangements, are implicitly disclosed herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Further, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

FIG. 1 is a high-level functional diagram of a system 10 for plain language summary draft generation using a data source and a language model in accordance with one or more preferred embodiments of the present invention. The system 10 includes a software platform 12, one or more clinical trial data repository 14, and an AI engine using a language model, which is preferably a large language model (LLM) 16. The software platform 12 preferably includes a front-end graphical user interface (GUI) and a back-end database. Users 18 utilize the front-end graphical user interface (GUI) to initiate plain language summary (PLS) documents 20, outline the content to be included therein, and identify the clinical trial that is to be summarized, wherein the outlined content includes dynamic tags to be replaced by AI-generated text and may also include data-driven tags to be replaced by elements of the study data. For each PLS document 20, the software platform 12 queries the data source in the repository 14 with respect to the identified clinical trial, and the data repository 14 returns the relevant study data and the elements corresponding to any data-driven tags. The software platform 12 then sends parameters for each respective AI tag (the input source data on which the text is to be based and a user-customized prompt) to the AI engine/LLM 16, which returns a written response for each one. The software platform 12 replaces each dynamic AI tag with the written response generated by the AI engine, and the resulting PLS draft document 20 is made available to the user(s) for review.

Figure 2:
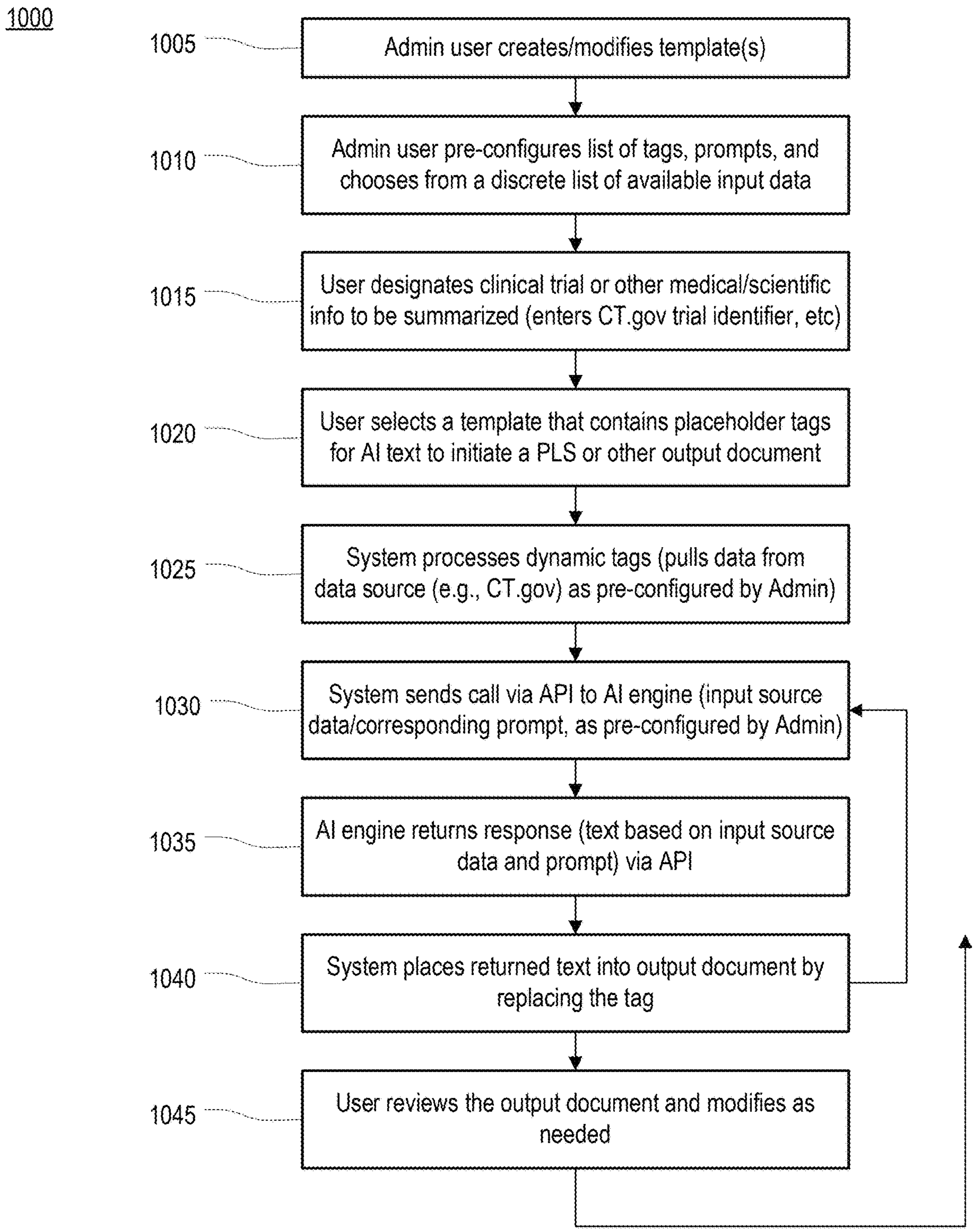
FIG. 2 is a flowchart illustration of a PLS draft generation process carried out by the system of FIG. 1 in accordance with one or more preferred embodiments of the present invention.

FIG. 2 is a flowchart illustration of a PLS draft generation process 1000 carried out by the system 10 of FIG. 1 in accordance with one or more preferred embodiments of the present invention. In at least some embodiments, the process 1000 includes one or more pre-configuration steps used to set up document templates, dynamic tags, and other preliminary aspects of PLS documents 20. Two such steps are illustrated at steps 1005 and 1010, but it will be appreciated that the steps themselves may be executed as part of a main process, or in some cases not at all, and that the order of the two illustrated steps is variable.

Figure 3:
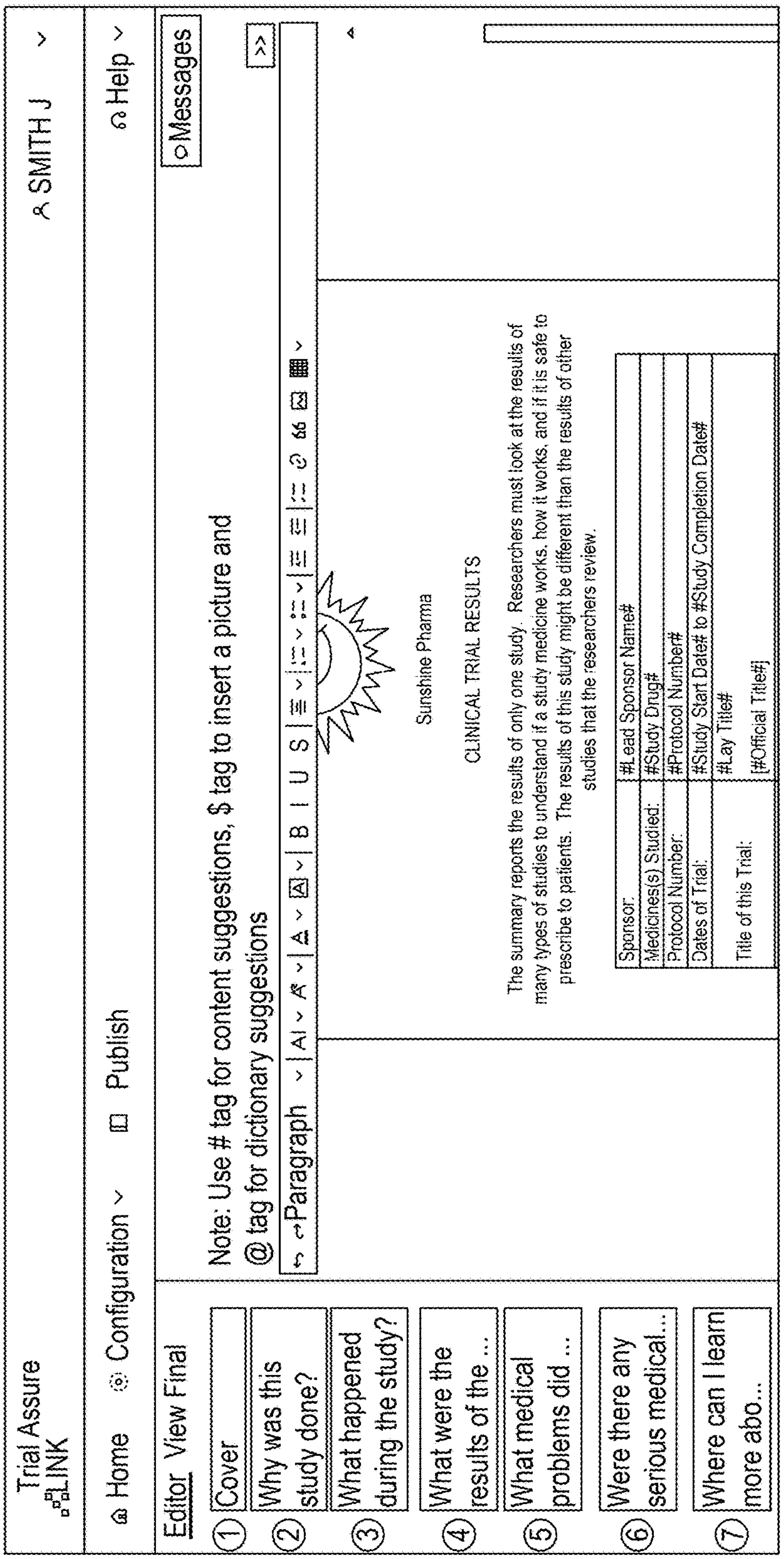
FIG. 3 is a screenshot illustration of an exemplary PLS template management interface for use in one or more preferred embodiments of the present invention.

At step 1005, a user creates and modifies one more templates for use in generating PLS documents 20. A tool for such functionality is preferably provided within the software platform 12, but in some cases a separate tool may be utilized, or a template may be created and edited in conventional word processing software. FIG. 3 is a screenshot illustration of an exemplary PLS template management interface 100 for use in one or more preferred embodiments of the present invention. In at least some embodiments, the user responsible for pre-configuration is an admin user with special privileges, but other arrangements may alternatively be utilized. The user can select an existing template for editing or can set up a new document template. In addition to placeholder tags for AI-written text (further described below), the template can include static text and images as well as placeholder tags for other dynamic data-driven elements, including dynamic text or other data, dynamic graphics/images, and other elements. Each tag includes a unique identifier that is formatted in a recognizable way, such as by placing the identifier between two hashtags ("#"). Several of these tags (e.g. "#Lead Sponsor Name#") are shown in the template illustrated in FIG. 3.

Figure 4:
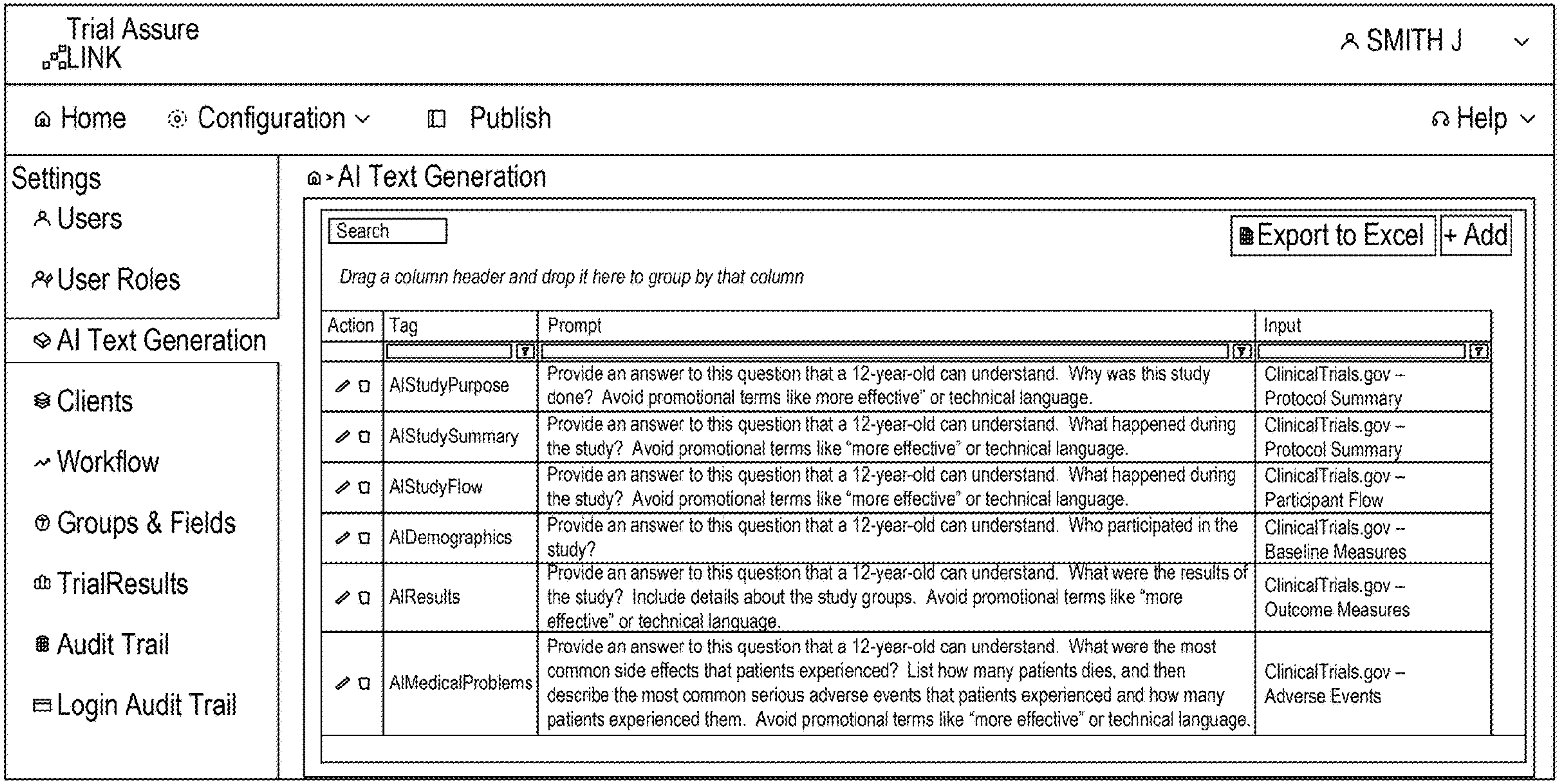
FIG. 4 is a screenshot illustration of an exemplary AI-generation tag management interface of the software platform of FIG. 1 illustrating a library of pre-configured parameter sets.

At step 1010, a user pre-configures AI-generation parameter sets for use in generating individual portions of plain language summary ("PLS") documents 20 for clinical trial results or the like. In this regard, FIG. 4 is a screenshot illustration of an exemplary AI-generation tag management interface 200 of the software platform 12 of FIG. 1 illustrating a library of pre-configured parameter sets. Each set of parameters is used to produce a portion of an output PLS document 20 using an AI engine/LLM 16 and place the portion thus produced in a designated location in the document 20. Each parameter set includes its unique tag identifier, an AI prompt, and the input source data section to be used by the AI engine/LLM 16 to produce the relevant document portion. As noted above, tags for the specific AI-generation parameters sets are used as placeholders in the documents 20 as they are being prepared. For each such tag, the corresponding AI prompt is used as instructions to the AI engine/LLM 16 to produce the desired portion of the output document 20, and the input source data defines the section of data that is retrieved from the source in the repository 14 and used by the AI engine/LLM 16 to generate the respective text that is inserted into the document 20. It will be appreciated that the parameter sets are generic in the sense that they are not based on a specific clinical trial but instead may be used with any available clinical study whose information is stored in a standardized structured data format. In this regard, the input source data is specified as a study record section: when a tag is used in a document 20 being generated for a particular study, the AI engine/LLM 16 uses the specified study record section for that study as its input source data.

As shown in FIG. 4, a library of pre-configured parameter sets may be created and modified as desired. In the illustrated embodiment, the interface for managing the tags (parameter sets) library is provided as part of a more comprehensive software application in the software platform 12, and is accessed via a "settings" dropdown menu in such application. More particularly, in the illustrated embodiment, the interface is accessed via an "AI Text Generation" section of the application settings. In at least some embodiments, the user 18 responsible for pre-configuration is an admin user with special privileges, but other arrangements may alternatively be utilized. In the illustrated embodiment, tags (parameter sets) may be created (by clicking a "+ Add" button), edited (by clicking a respective "pencil" icon), or deleted (by clicking a respective "trash-can" button). The tag (unique identifier) ("Tag" in FIG. 4) itself comprises a title (e.g. "AIStudyPurpose"); each tag is a free-form text field, but must be unique. The prompt ("Prompt" in FIG. 4) is an open-ended, free-form text field that provides instructions to the AI engine/LLM 16 (e.g. "Provide an answer to this question that a 12-year-old can understand. Why was this study done? Avoid promotional terms like 'more effective' or technical language"). The input source data ("Input" in FIG. 4) is a selection from a list of different data source options that are tailored to specific pieces of information. In the illustrated example, the input source data is one of the standard sections in which the studies in the database at ClinicalTrials.gov (sometimes referred to herein as "CT.gov") is organized, with the sections that are available being included in a dropdown, user-selectable list.

In at least some embodiments, when a user 18 is creating or modifying a document template at step 1005, the user 18 may utilize any of the AI tags from a library such as the one represented in FIG. 4. In some such embodiments, the user 18 may work back and forth between steps 1005 and 1010 to create or modify tags and use them in document templates.

With document templates and tags pre-configured at steps 1005 and 1010, a user (who may be a different type or class of user than the admin user of steps 1005 and 1010) may begin the process of preparing a PLS document 20 to be produced for a particular clinical trial (study). At step 1015, the user 18 designates the particular clinical trial that is to be summarized. For CT.gov, a specific clinical trial may be identified by its own unique identifier. Clinical trial data from other databases might be identified in a different manner.

Figure 5:
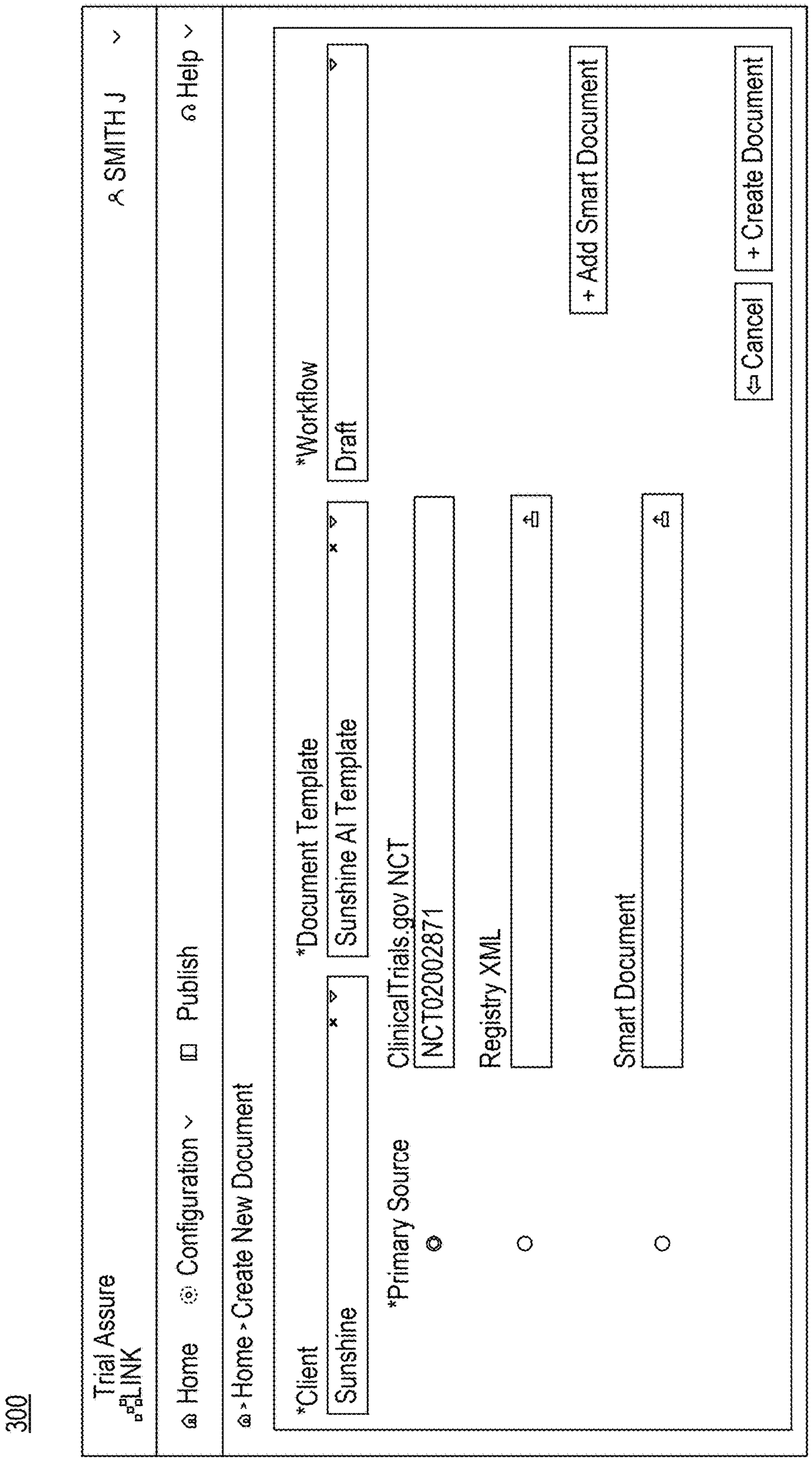
FIG. 5 is a screenshot illustration of a document creation interface of the software platform of FIG. 1.

At step 1020, a user selects a template that contains static elements and placeholder tags, including AI-generation tags for AI text, to initiate a PLS document 20, and inputs document information such as a title, author, due dates, and the like. In this regard, FIG. 5 is a screenshot illustration of a document creation interface 300 of the software platform 12 of FIG. 1. As shown therein, the user initiates a new PLS document 20 and selects the document template to use, as well as the data source 14 (in this example, a ClinicalTrials.gov record identified by its National Clinical Trials (NCT) identifier).

Next, the software platform 12 processes the various dynamic tags in the selected document template that relate directly to the structured data from the data source 14. The order in which these data-driven tags are processed may vary, but in one such processing step, shown at step 1025, the software platform 12 processes the various dynamic data-driven tags, including both dynamic text tags and dynamic graphics/images tags, and retrieves the text/data and graphics/images from the relevant sections of the particular clinical trial data being summarized. The software platform 12 then populates the output document 20 with the retrieved data and graphics/images as mapped and defined in the template configuration for the document 20. For example, the #StudyTitle# placeholder may be replaced with the "StudyTitle" element from the ClinicalTrials.gov record.

In another such processing step, the software platform 12 processes the various dynamic AI-generation tags in the template. For each AI-generation tag, as configured for example in the AI-generation tag management interface of FIG. 4, the software platform 12 sends a call to the AI engine/LLM 16 via the AI API, as shown at step 1030. In at least some embodiments, the call includes the prompt concatenated with the designated input source data. For example, a tag such as

#AIOutcomeMeasures# might be defined with a parameter set that includes the prompt "Summarize this information at a $6^{th}$ grade reading level," and might designate the input source data "ClinicalTrials.gov Outcome Measures section," in which case the software platform 12 would send the call "Summarize this information at a $6^{th}$ grade reading level [Outcome Measures]" where [Outcome Measures] represents the study data from the ClinicalTrials.gov Outcome Measures section for the applicable clinical study record. In at least some embodiments, the prompt and input source data are pre-configured by an admin user. For each call, the AI engine/LLM 16 then returns a response, via the AI API, in the form of text generated by the AI engine/LLM 16 based on the input source data and prompt for the call, as shown at step 1035.

Figure 6:
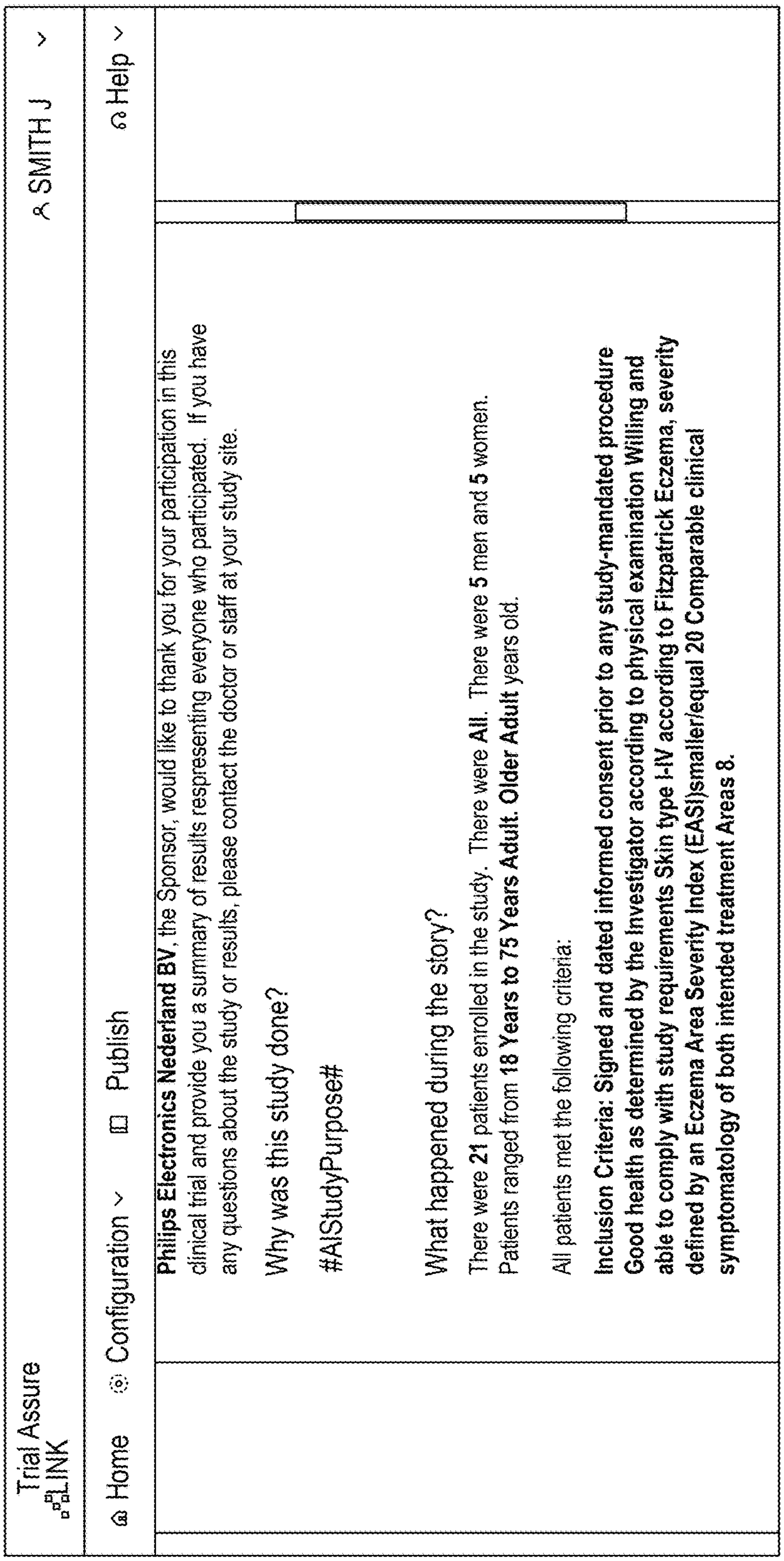
FIGS. 6 and 7 are screenshot illustrations of a document editor interface of the software platform of FIG. 1.
Figure 7:
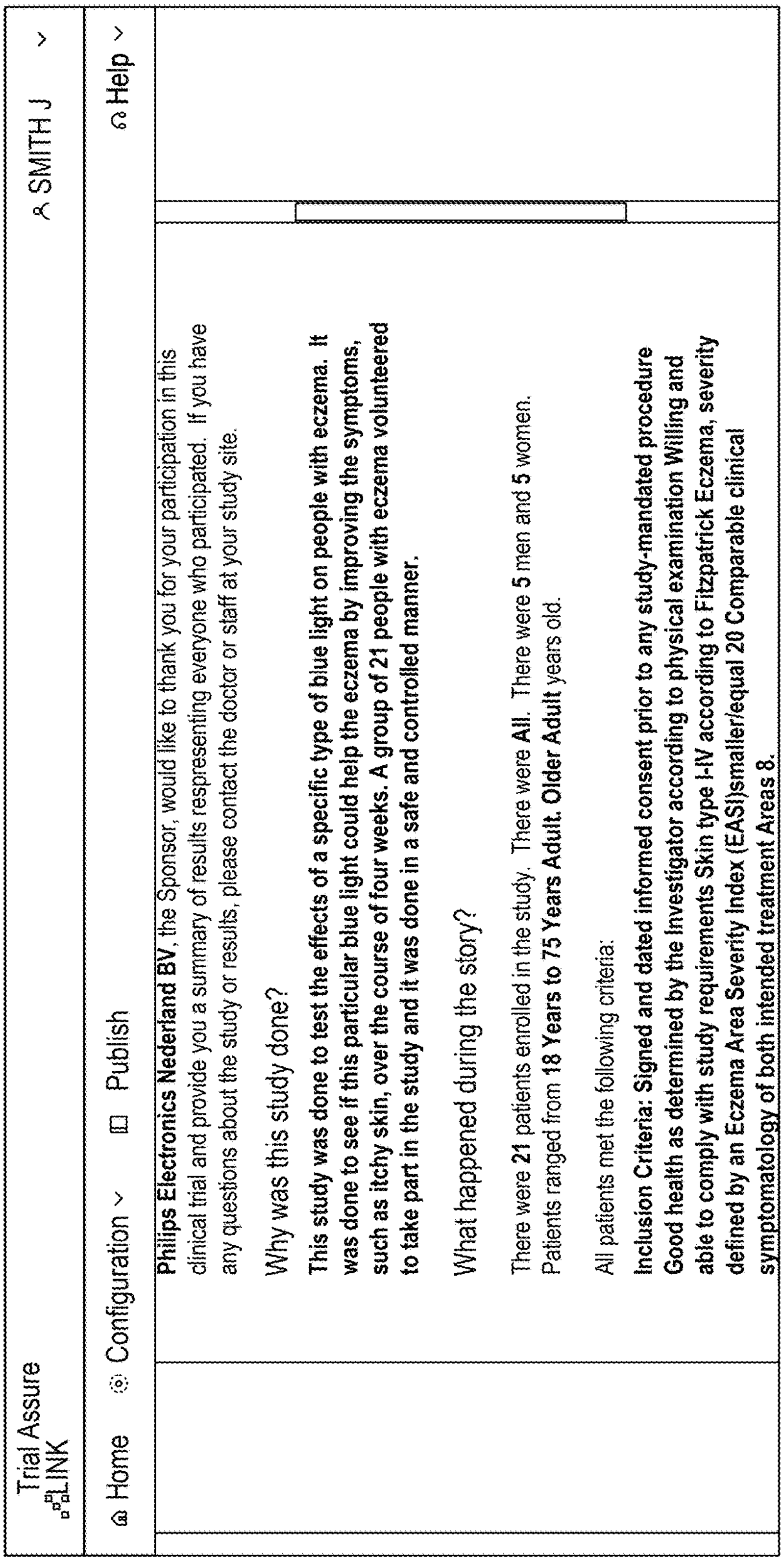

As AI-generated text is returned, it is placed in its tagged location in the document 20 at step 1040. For example, in the "Outcome Measures" example described above, #AIOutcomeMeasures# might be replaced by the text response in the example above. In this regard, FIGS. 6 and 7 are screenshot illustrations of a document editor interface 400 of the software platform 12 of FIG. 1. In the document editor, the placeholders are replaced by the content (shown in FIGS. 6 and 7 in bolded text) returned from the AI engine/LLM 16. For example, in FIG. 6, a tag "#AIStudyPurpose# has been entered in a section with the heading "Why was this study done?" while in FIG. 7, the tag has been replaced by a paragraph of text generated by the AI engine/LLM 16.

Figure 8:
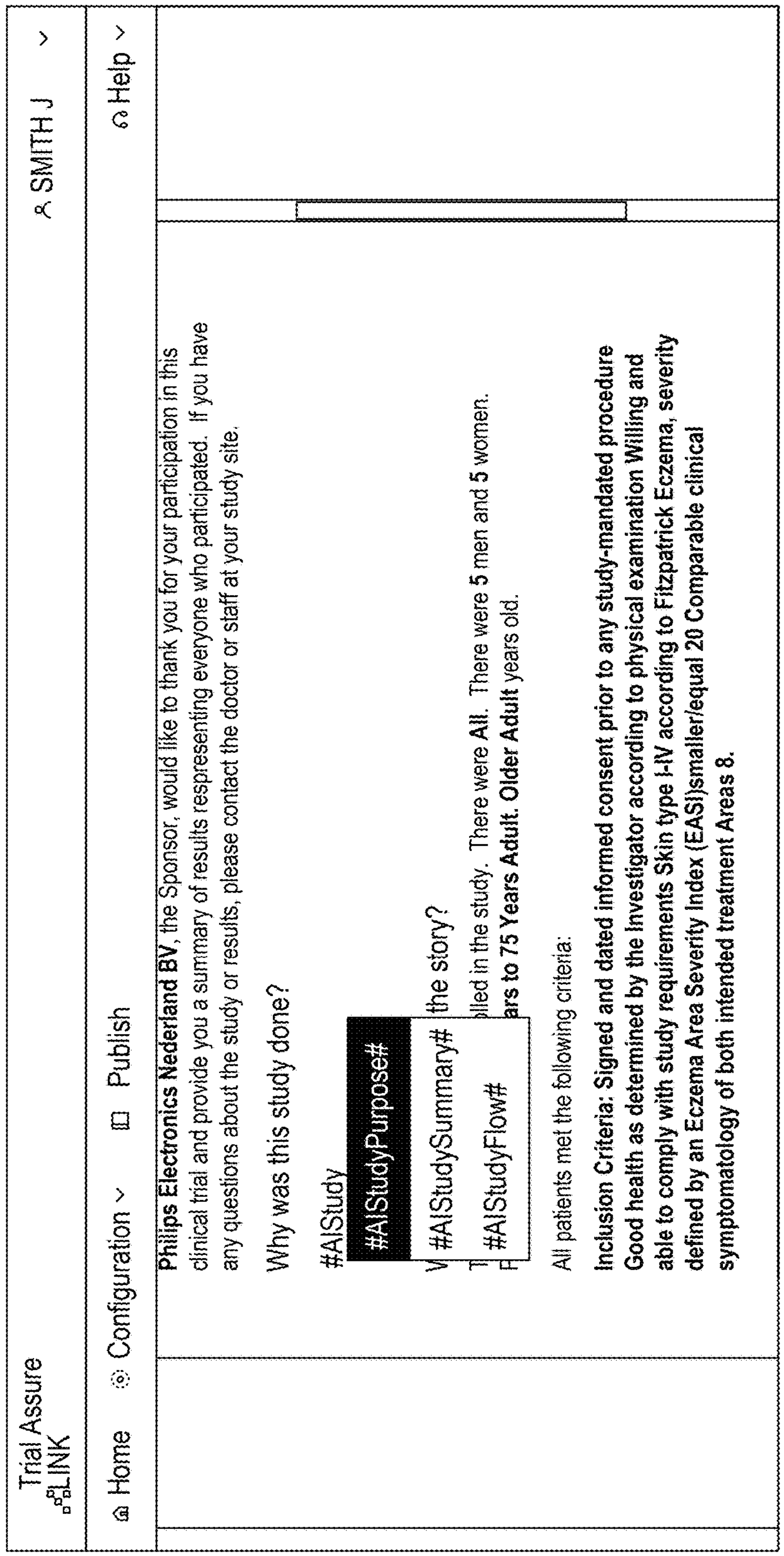
FIG. 8 is a screenshot illustrations of the document editor interface of the software platform of FIG. 1 showing alternative tag options.

In at least some embodiments (including that of FIG. 6), if further tags are desired, the user 18 can also dynamically add any of the AI tags that were configured in the application settings described above by entering a # and typing the name of the Tag (e.g. "AIStudyPurpose"). In this regard, FIG. 8 is a screenshot illustrations of the document editor interface 400 of the software platform 12 of FIG. 1 showing alternative tag options for the tag in the section with the heading "Why was this study done?"

In some embodiments, all of the tags in the document 20 are processed automatically by the software platform 12. In other embodiments, each tag is processed manually, wherein a user selects a tag, triggers a replacement function, and the software platform 12 automatically replaces the tag with the data, graphic/image, AI-generated text, or the like.

The final step 1045 illustrated in the process 1000 of FIG. 2 is for the user 18 to review the document 20 and modify as needed. In at least some embodiments, a user 18 can edit any text that existed in the template, compose new text, or modify any of the data-driven or AI-driven elements that were populated by the software platform 12. Review and modification can occur piecemeal, as the document 20 is populated by data, graphics/images, and AI-generated text, or may be deferred until a full draft is complete. In other words, in some embodiments, the document 20 is made available to the user 18 for editing only once all placeholder AI-generation tags have been replaced, while in other embodiments, the document 20 is available to the user 18 for review at all times, whether or not all AI-generation tags have been replaced.

In some embodiments, if a user 18 adds any further placeholder tags into the document 20 at this point, the software platform 12 automatically replaces the tag with the appropriate text. For example, the user 18 may dynamically enter the above-described #AIOutcomeMeasures# tag into the document 20. Assuming such tag is already configured as described, this tag will be automatically replaced with the returned text from the AI engine/LLM 16.

In some embodiments, the software platform 12 includes an iterative prompting engine, wherein a user 18 may review a response from the AI engine/LLM for a prompt and then modify the prompt to generate a new response. The updated response may then be plugged into the output document 20 wherever the corresponding tag is located. The iterative prompting engine may be presented to the user 18 in the format of a "chat," displayed via the GUI, between the user 18 and the AI engine 16 and the user 18, wherein the user 18 select which of the AI engine/LLM's responses are best suited for the output document 20.

Figure 9:
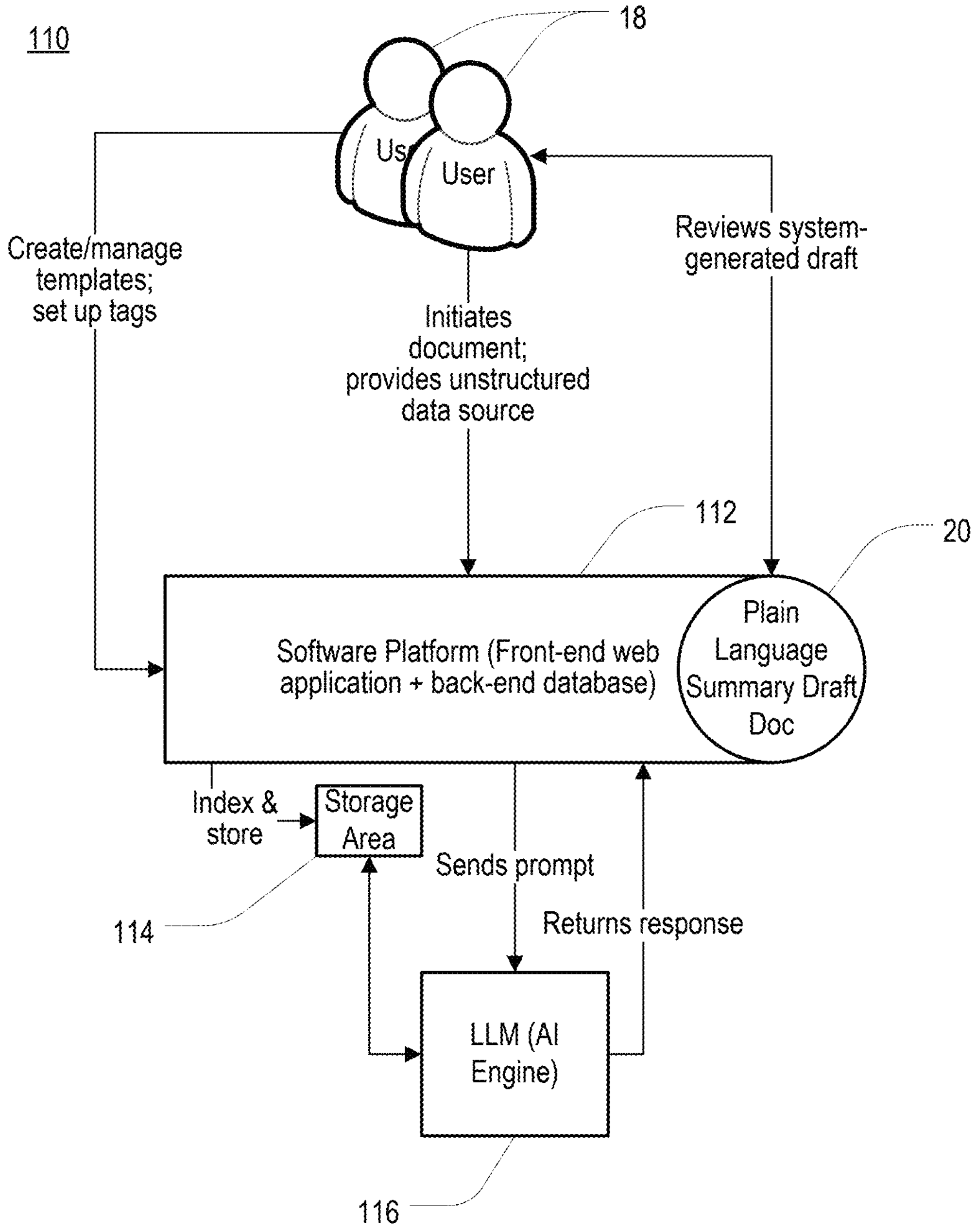
FIG. 9 is a high-level functional diagram of another system or plain language summary draft generation using a data source and a language model in accordance with one or more preferred embodiments of the present invention.

FIG. 9 is a high-level functional diagram of another system 110 for plain language summary draft generation using a data source and a language model in accordance with one or more preferred embodiments of the present invention. As with the system 10 of FIG. 1, the system 110 includes a software platform 112 and an AI engine using a language model, which is preferably once again a large language model (LLM) 116. Also similarly, the software platform 112 preferably includes a front-end graphical user interface (GUI) and a back-end database, and the users 18 utilize the front-end graphical user interface (GUI) to initiate plain language summary (PLS) documents 20 and to outline the content to be included therein, wherein the outlined content includes dynamic tags to be replaced by AI-generated text. The system 110 of FIG. 9, however, does not require a data repository 14. Instead, the system 110 utilizes data sources, including unstructured data sources, that are uploaded directly by users 18. The unstructured data sources are indexed and placed in a storage area 114 accessible to the AI engine/LLM 116. To produce a PLS document 20 corresponding to the uploaded data source, the software platform 112 sends parameters for each respective tag (the input source data on which the text is to be based and a user-customized prompt) to the AI engine/LLM 116, which "digests"/queries the indexed and stored data source and returns a written response for each one. Then, as with the software platform 12 of FIG. 1, the software platform 112 replaces each dynamic tag with the written response generated by the AI engine, and the resulting PLS draft document 20 is made available to the user(s) for review.

Figure 10:
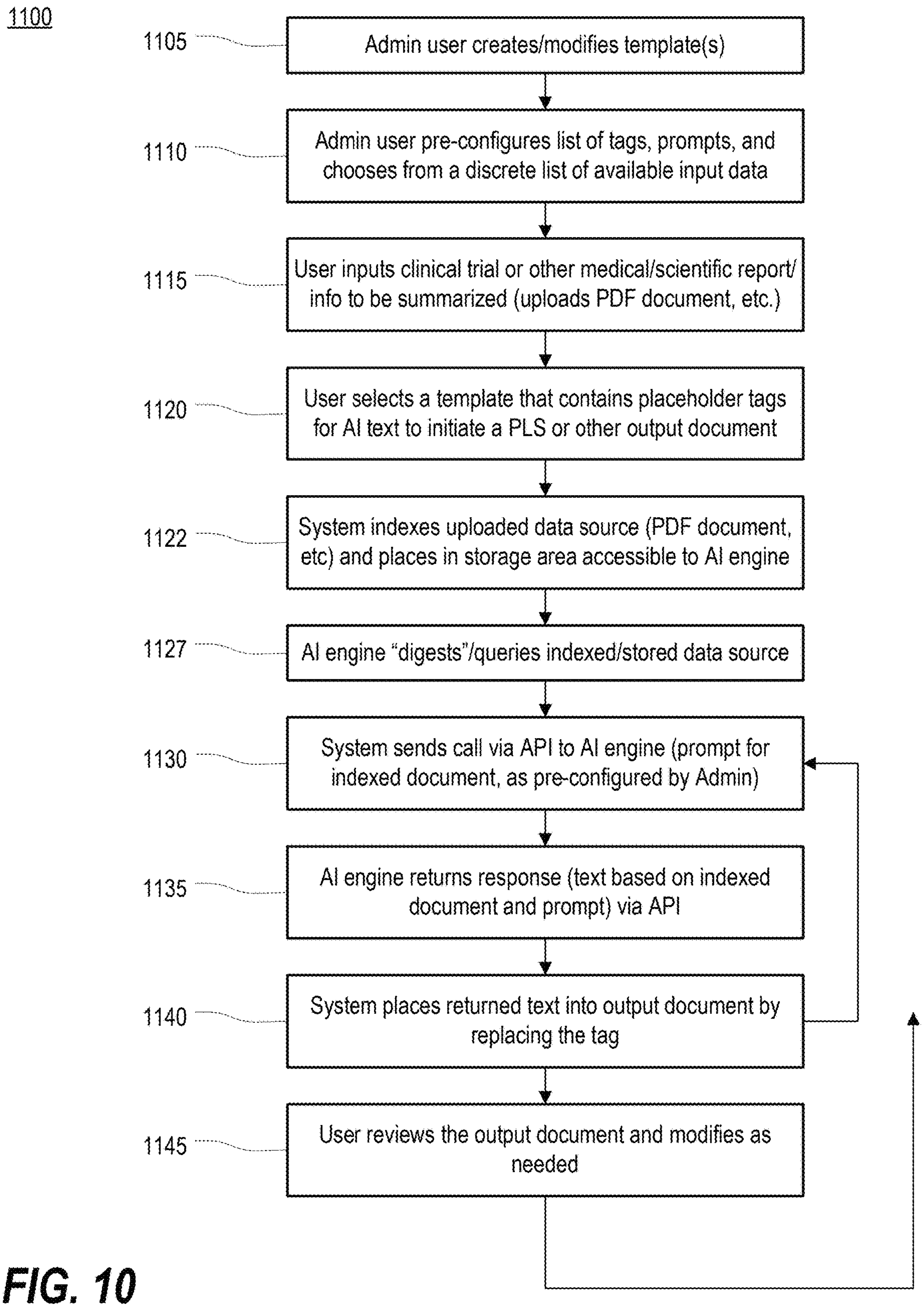
FIG. 10 is a flowchart illustration of a PLS draft generation process carried out by the system of FIG. 9 in accordance with one or more preferred embodiments of the present invention.

FIG. 10 is a flowchart illustration of a PLS draft generation process 1100 carried out by the system 110 of FIG. 9 in accordance with one or more preferred embodiments of the present invention. The process 1100 of FIG. 10 is similar in many respects to that of FIG. 2, but is not identical. Similarities and differences are highlighted hereinbelow.

As with the process of FIG. 2, in at least some embodiments, the process 1100 includes one or more pre-configuration steps used to set up document templates, dynamic tags, and other preliminary aspects of PLS documents 20. Two such steps are illustrated at steps 1105 and 1110, which in at least some embodiments are generally similar to steps 1005 and 1010 of FIG. 2, but it will be appreciated that the steps themselves may be executed as part of a main process, or in some cases not at all, and that the order of the two illustrated steps is variable.

With document templates and tags pre-configured at steps 1105 and 1110, a user (who may be a different type of user than the admin user of steps 1105 and 1110) may begin the process of preparing a PLS document 20 for a particular clinical trial (study). At step 1115, the user uploads a written data file, such as a document in a standard file format such as .pdf, into the software platform 112. In some embodiments, the document content may be organized in a standardized format such that dynamic data-driven tags may be utilized to organize and retrieve standard elements from the structured document, but in many embodiments the data source may be an unstructured data source and may relate, but is not necessarily required to relate, specifically to a clinical trial. Examples of documents that might be used include, without limitation, Protocol, Statistical Analysis Plan (SAP), Clinical Study Report (CSR), and other clinical documents and the like.

At step 1120, a user selects a template that contains placeholder tags for AI text to initiate a PLS document 20 (and, if applicable, data-driven tags) and inputs document information such as a title, author, due dates, and the like. In at least some embodiments, this step may be similar to step 1020 of FIG. 2.

Meanwhile, at step 1122, the software platform 112 indexes the uploaded data source and stores the indexed data source in the AI engine-accessible storage area 114, and as shown at step 1127, the AI engine/LLM 116 "digests" the indexed document, which can thereafter be interrogated by the software platform 112, via the AI engine/LLM 116, using prompts. In this sense, the AI engine/LLM 116 is able to pull from the entirety of a large document without information needing to be included in the prompt itself, and also without requiring pre-training on the study data.

As with the process 1000 of FIG. 2, the software platform 112 processes the various AI-generation tags in the template. For each AI-generation tag, the software platform 112 sends a call to the AI engine/LLM 116 via the AI API, as shown at step 1130. In at least some embodiments, the call need not include all the background data; the AI engine/LLM 116 interrogates the indexed document itself. For each call, the AI engine/LLM 116 then returns a response, via the AI API, in the form of text generated by the AI engine/LLM 116 based on the indexed document and prompt for the call, as shown at step 1135. Then, as AI-generated text is returned, it is placed in its tagged location in the document 20 at step 1140 in at least somewhat similar manner to step 1040 in FIG. 2.

In some embodiments, all of the tags in the document 20 are processed automatically by the software platform 112. In other embodiments, each tag is processed manually, wherein a user selects a tag, triggers a replacement function, and the software platform 112 automatically replaces the tag with the AI-generated text, or where applicable, text/data or graphics/images directly from the structured data source.

The final step 1145 illustrated in the process 1100 of FIG. 10 is for the user to review the document 20 and modify as needed. In at least some embodiments, the user can edit any text that existed in the template, compose new text, or modify any of the data-driven or AI-driven elements that were populated by the software platform 12. Review and modification can occur piecemeal, as the document 20 is populated by data, graphics/images, and AI-generated text, or may be deferred until a full draft is complete. In some embodiments, if the user adds any further placeholder tags into the document 20 at this point, the software platform 12 automatically replaces the tag with the appropriate text. For example, the user may dynamically enter the above-described #AIOutcomeMeasures# tag into the document 20. Assuming such tag is already configured as described, this tag will be automatically replaced with the returned text from the AI engine/LLM 16.

In some embodiments, when an output document 20 is first created, the software platform 12,112 sends a call or calls to the AI engine/LLM 16,116, via the AI API, with respect to every tag in the library of tags, whether or not they exist in the document 20, and makes use of its own database to store the responses for all of the tags when received back from the AI engine/LLM 16,116. This approach avoids the need to make a unique call via the AI API if an additional tag from the library is dynamically added to the document 20: so long as the tag was preconfigured, the text will have already been generated and stored in the database and thus immediately available when the tag is added.

In at least some embodiments, one or both systems 10,110 described hereinabove may be used to produce PLSs for clinical trial results in various formats from a variety of sources, including based on for clinical trial results stored standard databases 14 (like those available at ClinicalTrials.gov) as well as a variety of other sources, including unstructured clinical trial results, clinical trial protocols, clinical trial publications in scientific journals, and the like. In at least some embodiments, a system (not illustrated) may incorporate elements of both of the illustrated systems 10,110. In at least some embodiments, PLSs may also be produced for other medical, pharmaceutical, and/or other scientific research reports and other information.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claim(s) appended hereto and the equivalents thereof.

What is claimed is:

1. A method providing a technical solution to the technical problem of using a software platform to control an artificial intelligence (AI) interface to produce plain language summaries (PLSs) for clinical trial data sources, comprising:

(a) effecting display, to a first user who has utilized a web browser loaded on a first device to navigate to a uniform resource locator, of a PLS template management interface prompting the first user to create a template for a PLS;

(b) receiving data corresponding to input by the first user corresponding to creation of a first PLS output document template;

(c) creating the first PLS output document template based on the received data;

(d) effecting display, to the first user in the web browser loaded on the first device, of an editor tool for editing the first PLS output document template;

(e) receiving data corresponding to input by the first user defining fields and sections of the first PLS output document template;

(f) effecting display, to a second user who has utilized a web browser loaded on a second device to navigate to a uniform resource locator, of a dynamic tag management interface, for managing placeholder tags for AI-generated text, prompting the second user to create a dynamic AI-text tag for use in PLS output document templates;

(g) receiving data corresponding to input by the second user corresponding to creation of a first dynamic AI-text tag;

(h) creating the first dynamic AI-text tag based on the received data;

(i) effecting display, to the second user in the web browser loaded on the second device, of an editor tool for configuring the first dynamic AI-text tag;

(j) receiving data corresponding to input by the second user defining a parameter set for the first dynamic AI-text tag, the parameter set including at least a unique tag identifier and an AI prompt;

(k) storing the first dynamic AI-text tag for subsequent use in PLS output document templates for producing PLSs for clinical trial data sources;

(l) while effecting display, to the first user in the web browser loaded on the first device, of the editor tool for editing the first PLS output document template, prompting the first user to select one or more dynamic AI-text tags for adding to the first PLS output document template;

(m) receiving data corresponding to input by the first user selecting at least the first dynamic AI-text tag and placing it a first location in the first PLS output document template;

(n) adding the one or more dynamic AI-text tags, including the first dynamic AI-text tag, to the first PLS output document template in the first location in the first PLS output document template;

(o) storing the first PLS output document template for subsequent use in producing PLSs for clinical trial data sources;

(p) effecting display, to a third user who has utilized a web browser loaded on a third device to navigate to a uniform resource locator, of a PLS document creation interface prompting the third user to initiate a PLS output document;

(q) receiving data corresponding to input by the third user corresponding to initiation of a first PLS output document;

(r) creating the first PLS output document based on the received data;

(s) effecting display, to the third user in the web browser loaded on the third device, of an editor tool for prompting the third user to identify input clinical trial source data and select a PLS output document template for the first PLS output document;

(t) receiving data corresponding to input by the third user identifying designated input clinical trial source data and selecting the first PLS output document template for the first PLS output document;

(u) receiving data corresponding to instruction by the third user to generate the first PLS output document;

(v) thereafter, generating a draft of the first PLS output document, wherein such generating step includes, for each of the one or more dynamic AI-text tags in the first PLS output document template:

(i) sending the AI prompt to an AI engine with language model, (ii) via the AI engine with language model, processing the AI prompt against the designated input clinical trial source data to generate draft plain language for use in the draft of the first PLS output document, (iii) returning the generated draft plain language from the AI engine with language model, and (iv) replacing the respective dynamic AI-text tag in the draft of the first PLS output document with the draft plain language returned from the AI engine with language model; and (w) effecting display, to the third user in the web browser loaded on the third device, of a completed version of the draft first PLS output document.

2. The method of claim 1, wherein the first user and the second user are the same user.

3. The method of claim 1, wherein the first user and the third user are the same user.

4. The method of claim 1, further comprising steps of:

effecting display, to the second user who has utilized a web browser loaded on the second device to navigate to a uniform resource locator, of the dynamic tag management interface, for managing placeholder tags for AI-generated text, prompting the second user to create additional dynamic AI-text tags for use in PLS output document templates;

receiving data corresponding to input by the second user corresponding to creation of additional dynamic AI-text tags;

creating the additional dynamic AI-text tags based on the received data;

effecting display, to the second user in the web browser loaded on the second device, of the editor tool for configuring the additional dynamic AI-text tags;

receiving data corresponding to input by the second user defining a parameter set for each of the additional dynamic AI-text tags, each respective parameter set including at least a unique tag identifier and an AI prompt;

storing the additional dynamic AI-text tags for subsequent use in PLS output document templates for producing PLSs for clinical trial data sources; and effecting display, to the first user in the web browser loaded on the first device, a library of stored dynamic AI-text tags for use by the first user in selecting the one or more dynamic AI-text tags for adding to the first PLS output document template.

5. The method of claim 1, further comprising:

effecting display, to a fourth user who has utilized a web browser loaded on a fourth device to navigate to a uniform resource locator, of the PLS document creation interface prompting the fourth user to initiate a PLS output document;

receiving data corresponding to input by the fourth user corresponding to initiation of a second PLS output document;

creating the second PLS output document based on the received data;

effecting display, to the fourth user in the web browser loaded on the fourth device, of the editor tool for prompting the fourth user to identify input clinical trial source data and select a PLS output document template for the second PLS output document;

receiving data corresponding to input by the fourth user identifying designated input clinical trial source data and selecting the first PLS output document template for the second PLS output document;

receiving data corresponding to instruction by the fourth user to generate the second PLS output document;

thereafter, generating a draft of the second PLS output document by, wherein the generating step includes, for each of the one or more dynamic AI-text tags in the second PLS output document template:

(i) sending the AI prompt to an AI engine with language model, (ii) via the AI engine with language model, processing the AI prompt against the designated input clinical trial source data to generate draft plain language for use in the draft of the second PLS output document, (iii) returning the generated draft plain language from the AI engine with language model, and (iv) replacing the respective dynamic AI-text tag in the draft of the second PLS output document with the draft plain language returned from the AI engine with language model; and effecting display, to the fourth user in the web browser loaded on the fourth device, of a completed version of the draft second PLS output document.

6. The method of claim 5, wherein the third user and the fourth user are the same user.

7. The method of claim 5, wherein the third user and the fourth user are different users.

8. The method of claim 1, wherein the input clinical trial source data is structured data.

9. The method of claim 8, wherein the structured data is stored in a standardized format in a clinical trial data repository.

10. The method of claim 9, wherein the parameter set for each dynamic AI-text tag further includes a section of data from the structured input clinical trial source data, and wherein generating a draft of the first PLS output document further includes, for each of the one or more dynamic AI-text tags in the second PLS output document template, sending the section of data to the AI engine with language model as part of the AI prompt.

11. The method of claim 8, further comprising:

effecting display, to the second user who has utilized a web browser loaded on the second device to navigate to a uniform resource locator, of a dynamic tag management interface, for managing placeholder tags for data-driven elements of the structured input clinical trial source data;

prompting the second user to create a dynamic source data-driven tag for use in PLS output document templates;

receiving data corresponding to input by the second user corresponding to creation of a first dynamic source data-driven tag;

creating the first dynamic source data-driven tag based on the received data;

effecting display, to the second user in the web browser loaded on the second device, of an editor tool for configuring the first dynamic source data-driven tag;

receiving data corresponding to input by the second user defining a parameter set for the first dynamic source data-driven tag, the parameter set including at least a unique tag identifier and a specific structured element to be retrieved from the structured input clinical trial source data and substituted for the first dynamic source data-driven tag;

storing the first dynamic source data-driven tag for subsequent use in PLS output document templates for producing PLSs for clinical trial data sources; and while effecting display, to the first user in the web browser loaded on the first device, of the editor tool for editing the first PLS output document template, prompting the first user to select one or more dynamic source data-driven tags for adding to the first PLS output document template.

12. The method of claim 11, wherein the step of generating the draft of the first PLS output document includes, for each of the one or more dynamic source data-driven tags in the first PLS output document template:

(i) retrieving the specific structured element from the designated input clinical trial source data, and (ii) replacing the respective dynamic source data-driven tag in the draft of the first PLS output document with the retrieved structured element.

13. The method of claim 11, wherein the specific structured element is specific text, specific data, a specific graphic, or a specific image.

14. The method of claim 1, wherein the input clinical trial source data is uploaded by the third user.

15. The method of claim 14, wherein the input clinical trial source data is unstructured data.

16. The method of claim 15, further comprising a step of indexing the uploaded input clinical trial source data and placing the indexed input clinical trial source data in a storage area accessible to the AI engine, and wherein generating a draft of the first PLS output document further includes, for each of the one or more dynamic AI-text tags in the second PLS output document template, querying the indexed input clinical trial source data by the AI engine with language model.

17. The method of claim 14, wherein the input clinical trial source data is in a document of a standard file type.

18. The method of claim 1, wherein the first PLS output document template is one of a plurality of PLS output document templates stored in a library, and wherein the step of effecting display, to the third user in the web browser loaded on the third device, of an editor tool includes effecting display of the library of PLS output document templates for prompting the third user to select one of the PLS output document templates, of the plurality of PLS output document templates, for the first PLS output document.

* * * * *